United States Patent
Lienard et al.

(10) Patent No.: US 7,440,790 B2
(45) Date of Patent: Oct. 21, 2008

(54) METHOD AND APPARATUS FOR MONITORING CARDIAC ACTIVITY

(75) Inventors: Jean Lienard, Igny (FR); Regis Vaillant, Villebon sur Yvette (FR)

(73) Assignee: General Electric Company, Schenectady, NY (US)

( * ) Notice: Subject to any disclaimer, the term of this patent is extended or adjusted under 35 U.S.C. 154(b) by 328 days.

(21) Appl. No.: 11/114,378

(22) Filed: Apr. 26, 2005

(65) Prior Publication Data

US 2005/0288570 A1    Dec. 29, 2005

(30) Foreign Application Priority Data

Jun. 24, 2004    (FR)    ................................ 04 06902

(51) Int. Cl.
| | |
|---|---|
| *A61B 5/05* | (2006.01) |
| *A61B 6/00* | (2006.01) |
| *A61B 5/02* | (2006.01) |
| *G06K 9/00* | (2006.01) |
| *G01N 23/04* | (2006.01) |

(52) U.S. Cl. ........................ 600/407; 600/436; 600/508; 382/128; 378/62

(58) Field of Classification Search .................. 600/407, 600/428; 382/130; 378/8, 95
See application file for complete search history.

(56) References Cited

U.S. PATENT DOCUMENTS

| | | | | |
|---|---|---|---|---|
| 4,360,030 | A * | 11/1982 | Citron et al. ................. | 600/515 |
| 7,020,511 | B2 * | 3/2006 | Boyd et al. .................. | 600/428 |
| 7,092,482 | B2 * | 8/2006 | Besson ........................ | 378/37 |
| 2005/0002549 | A1 | 1/2005 | Vaillant et al. | |

FOREIGN PATENT DOCUMENTS

| | | |
|---|---|---|
| FR | 2 848 093 A | 6/2004 |
| JP | 2000/225115 A | 8/2000 |
| WO | WO 01/67960 A | 9/2001 |
| WO | WO 02/26125 A | 4/2002 |

* cited by examiner

*Primary Examiner*—Eric F Winakur
*Assistant Examiner*—Michael T. Rozanski
(74) *Attorney, Agent, or Firm*—GE Global Patent Operation

(57) ABSTRACT

A method and apparatus for monitoring cardiac activity starting from a series of images of the heart made by X-rays. Attenuation of the X-rays is sampled on an area subject to repetitive thickenings of at least one wall of the heart, and a repetitive attenuation signal is interpreted as a signal representative of the heart activity.

28 Claims, 5 Drawing Sheets

METHOD AND APPARATUS FOR MONITORING CARDIAC ACTIVITY

CROSS-REFERENCE TO RELATED APPLICATIONS

This application claims the benefit of a priority under 35 USC 119(a)-(d) to French Patent Application No. 04 06902 filed Jun. 24, 2004, the entire contents of which are hereby incorporated by reference.

BACKGROUND OF THE INVENTION

This invention relates to monitoring of cardiac activity, e.g., movement, and in particular by means other than direct recording of the electrical activity of the heart. It is important to know the activity of the heart (particularly the rate and regularity of heart beats) in different situations when normal methods of producing an electrocardiogram are not available or is difficult to use. An electrocardiogram (ECG) is used firstly to diagnose a heart disease or heart damage, but also to evaluate the effects of a heart treatment or activity regulation device (pacemaker).

The electrocardiogram is often used in parallel with acquisition of angiographic images, particularly during surgical operations. Apart from these medical applications, the electrocardiogram signal is also used for the treatment of cardiovascular angiography images. It makes it easy to identify images corresponding to the same phase in different heart cycles. Thus, two synchronous images may be obtained and subtracted from each other, thus eliminating effects of contrast due to unimpregnated tissues, and thereafter by showing contrasts due solely to impregnation from injected contrast material that appeared between the two cycles.

In case the electrocardiogram is not accessible or missing in the angiographic system, it is necessary to provide an equivalent signal form from the available information, i.e., images. An embodiment of the present invention is to circumvent the lack of a true electrocardiogram signal or provide an alternative to the electrocardiogram signal.

BRIEF DESCRIPTION OF THE INVENTION

An embodiment of the invention provides a signal equivalent to the electrocardiogram in the absence of typical means used for this purpose, in other words from a single sequence of images acquired by an imaging system. In particular, an embodiment of the invention relates to projection imaging systems, and particularly X-ray systems. In particular, an embodiment of the invention provides such a signal with a particularly high reliability.

An embodiment of the invention is a method and apparatus for heart activity monitoring starting from a series of angiographic images made by X-rays. Attenuation of X-rays is sampled on an area subject to repetitive thickenings of at least one wall of the heart, and a repetitive attenuation signal corresponding to thickenings is interpreted as a signal representative of the heart activity.

BRIEF DESCRIPTION OF THE DRAWINGS

Other characteristics, purposes and advantages of the invention and embodiment thereof will become clearer after reading the following detailed description given with reference to the appended figures, wherein.

DETAILED DESCRIPTION OF THE INVENTION

Figure 1A:
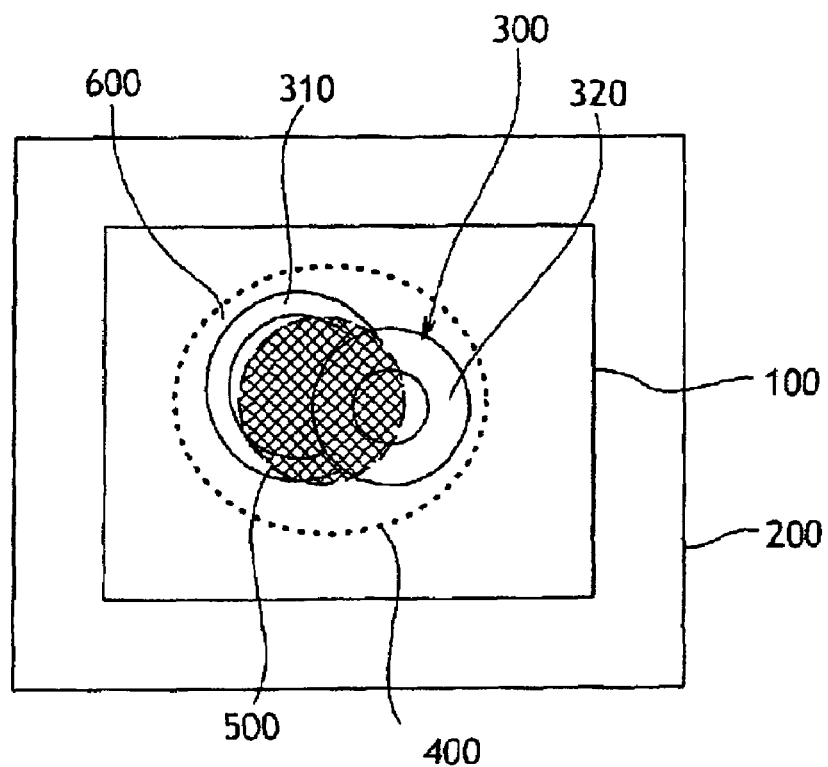
FIGS. 1A and 1B are exposures used in an embodiment of the invention; one is diagrammatic and the other is more realistic.
Figure 1B:
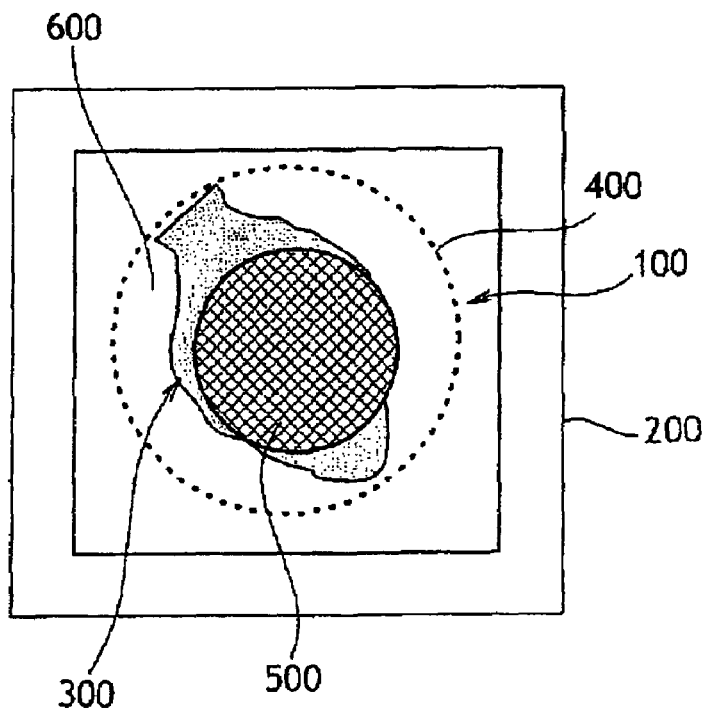

An embodiment of the invention obtains a series of images like those illustrated in FIG. 1. Each image is inscribed within an acquisition field 100 of the rectangular type corresponding approximately to the entire display area of the screen 200. The heart 300 is approximately at the center of the acquisition field shown in FIG. 1A in the form of two adjacent rings 310 and 320, these rings 310 and 320 diagrammatically representing the right ventricle 310 and the left ventricle 320. In FIG. 1B, which conforms more to the projective nature of the imaging system, the heart is represented as a gray elliptical shape.

Obviously, these representations are very diagrammatic, since the image of the heart can have different orientations depending on the position of a sensor and a radiation source, such as X-rays.

Moreover, in practice the view is not a sectional view like that shown diagrammatically in this case in FIG. 1A, but is a projective view like that shown in FIG. 1B. In other words, each pixel of the acquisition field is a projection of a set of attenuations encountered along an axis that connects the pixel considered to the X-ray source.

There are variations in the thickness of heart walls, in other words variations of the quantity of tissue through which all the projection axes of a given sampling area pass. In this context, we are interested in variations of wall thicknesses on an area covering part of the heart that is delimited approximately by the outside shape of the heart. In this case, this area is inscribed within a circle 400, shown in dashed lines in FIGS. 1A and 1B, that is chosen to approximately surround the image of the heart. It is only slightly larger than the projection of the heart, such that it is approximately flush with the sidewalls of the heart.

The attenuation of radiation in this area is transformed into an equivalent water depth, in other words, the water depth that outputs the same intensity pixel as that displayed on the screen in the area in question. This is done using Lambert's law that defines the attenuation of a monochromatic X-ray as follows:

$$I = I_{max}^{-\mu H} \Rightarrow H - \frac{1}{\mu}[\log(I_{max}) - \log(I)]$$

where H is the equivalent water depth, $\mu$ is the attenuation coefficient and $I_{max}$ is the maximum intensity of the image, where μ is equal to about 0.02 mm$^{-1}$, for linear attenuation of water under an exposure at 80 kV.

The intensity I is the average intensity sampled at each instant inside a monitoring area, in other words in the area affected by variations in the thickness of the walls of the heart. The monitoring area 600 will be called a Region Of Interest (ROI).

In this example, the imaging apparatus is provided with image intensity slaving means, in a manner conventional in itself. The purpose of these slaving means is to maintain a constant average intensity in an area that also covers a non-negligible part of the heart. This area is shown cross-hatched as reference 500 in FIGS. 1A and 1B. It is a central disk with a dimension conventionally less than the image of the heart on the screen. The slaving means measures the average intensity in the disk 500 by integrating all pixels on this disk, and then modulates the intensity of X-rays on emission, such that this average intensity reaches a predefined set value. In other words, the central disk 500 only has very small intensity variations, even within a heart cycle, since the slaving loop acts in a real time to keep the intensity constant. The central slaving disk 500 is extracted from the area used for observation of attenuation variations. Typically, this eliminated part will cover 50% of the projection field 100.

Thus, the area in which the thickness of the wall passed through is monitored, is limited to a ring 600, delimited on the outside by the previously described circle 400, and delimited on the inside by the periphery of slaved disk 500. Ring 500 is precisely the area in which the greatest variations of wall thickness occur, since it transversely covers the walls of the left and right ventricles. In other words, ring 600 covers walls for which the variable thickness forms a mask with a variable size in front of the X-ray beam. In other words, the sampling area is placed such that the heart has at least one wall for which the projected thickness has a variable range in the sampling area.

Figure 2:
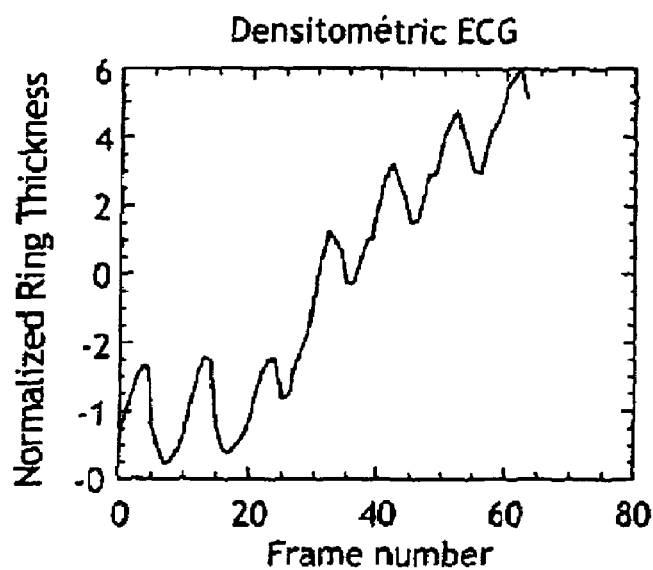
FIG. 2 illustrates the variation of a signal representative of the heart activity obtained in this embodiment.

The average intensity integrated on all pixels in ring 600 varies with time as shown in FIG. 2, in which each peak corresponds to the systolic phase of a beat. These peaks are distributed with a generally increasing variation, since in this case the test was done while a contrast material was being injected. This contrast material is used for other purposes, and is not necessary for implementation of embodiments of the invention. Thus, the water depth signal resulting from this processing has a quasi-periodic variation superposed to the gradual variation due to injection of the contrast material into the epicardial artery and its perfusion into the myocardium.

The plot obtained by an intensity reading of this type is particularly meaningful. The plot in FIG. 2 is used by a calculation step that comprises calculating a correlation function expressed by the following equation:

$$R(k) = \sum_t S(t) \cdot S(t+k)$$

In this equation, R is the autocorrelation function, S is the time signal in FIG. 2, t is the time as integrated on this signal and k is the variable of the autocorrelation function, also expressed as a time.

Figure 3:
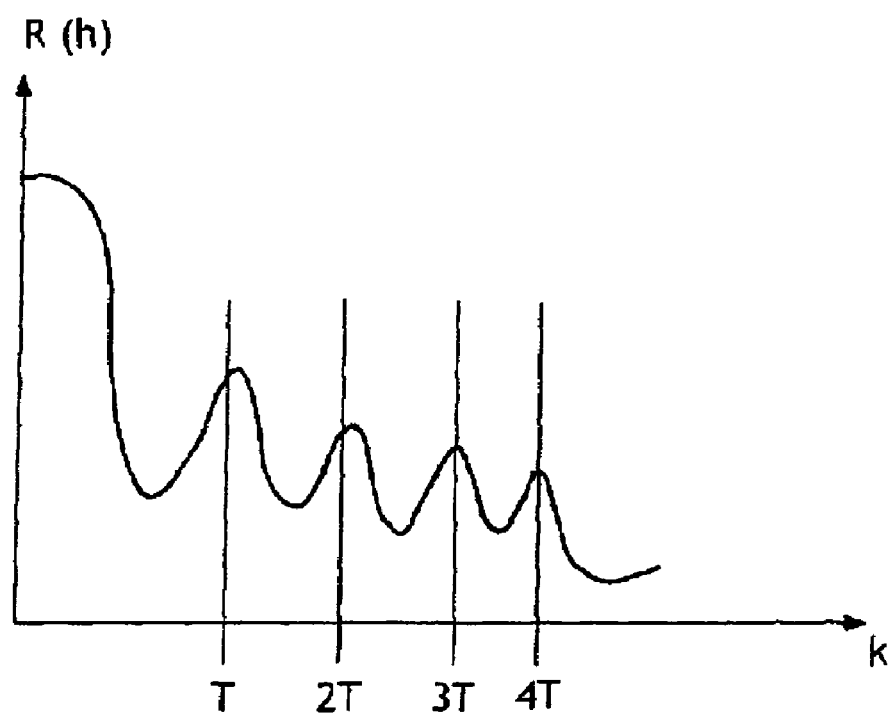
FIG. 3 represents a correlation plot produced from the signal representative of the heart activity.

The plot of the autocorrelation function, as shown in FIG. 3, is itself in the form of a series of successive peaks, the first of which is positioned at an average value of the periods of the heart signal. Subsequent peaks are multiples of the average period.

The function outputs are a particularly precise average value T for the period. This average value S is used in a subsequent step in which T is compared with the duration of each beat encountered on the plot in FIG. 2. Thus, individual elongations or shortenings of each beat are identified, which helps to identify each given phase of the heart configuration during the different beats. In other words, elongations and shortenings of periods identified by comparison with this average value T provides a means of extracting synchronous images belonging to different beats. By subtraction between these synchronous images, contrasts due to tissues not impregnated by the contrast material, in other words tissues with lesser interest and particularly tissues other than heart tissues, are eliminated.

Figure 4:
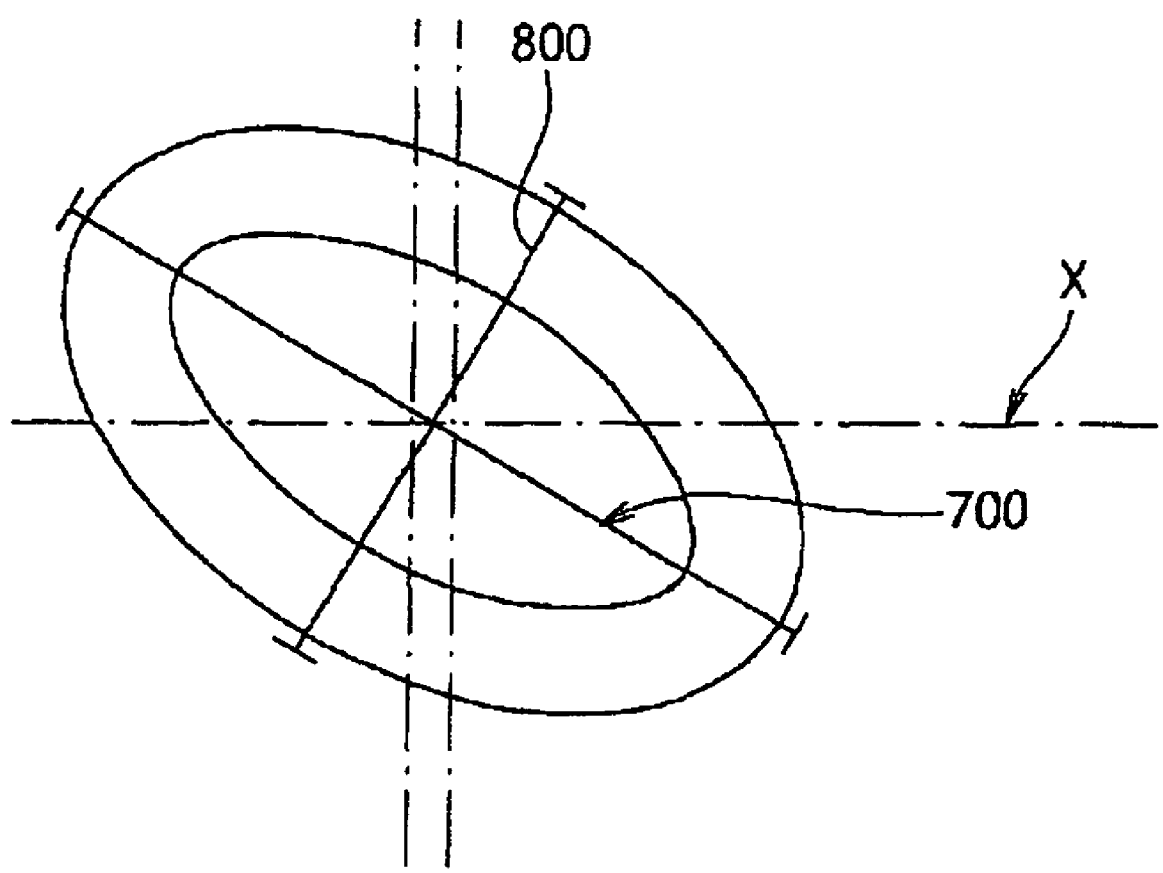
FIG. 4 is an exposure shown in another embodiment of the invention.

In another embodiment of the invention, the intensity reading is in the form of an attenuation profile produced transversely to at least one wall of the heart. To achieve this, attenuation values used will be restricted to pixel segments directed transversely to the image of the heart. Thus in FIG. 4, a first segment 700 is a segment specifically oriented at 30° from a main longitudinal axis X of the heart. A second segment is a segment 800, positioned at 60° from the longitudinal axis X.

These orientations at 30 and 60° are chosen to intersect the walls of the ventricles and to obtain profiles independent of the orientation of the mechanical arc supporting the X-ray imaging device.

Therefore, the sampling area (the segment considered) is positioned such that the heart has at least one wall for which the range of the projected thickness is variable within the sampling area. Intensities of pixels are recorded on each of these segments 700 and 800, and these intensities are displayed as a function of the degree of progress on this segment considered (FIG. 5) in the form of a transverse attenuation profile of the heart. More specifically, an average profile 900 is produced by taking the average of the two profiles for segments 700 and 800. In this case, this average profile 900 as shown on FIGS. 5 and 6 has two main elevations 910 and 920. Each corresponds to the intersection of the sampling segment and the walls of the left ventricle, in which the thickness passed through is particularly high. This profile 900 also has a significantly lower additional elevation 930, corresponding to a wall of the right ventricle.

Figure 5:
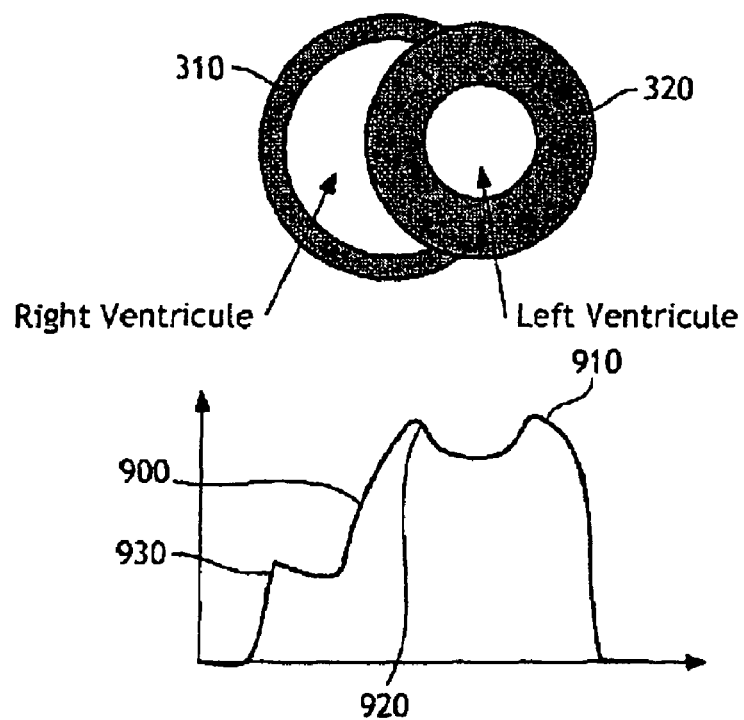
FIG. 5 represents a radiation attenuation profile, corresponding to a diagrammatic section through the heart in the diastolic phase.
Figure 6:
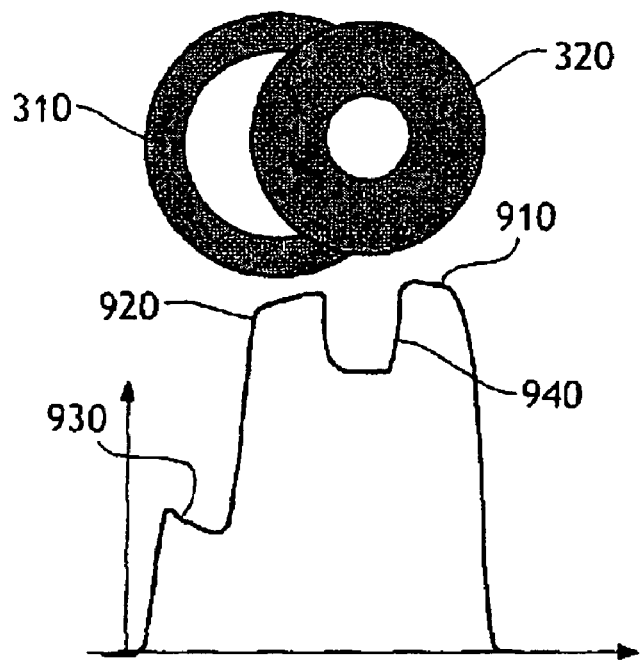
FIG. 6 represents a radiation attenuation profile, corresponding to a diagrammatic section through the heart in the systolic phase.

Significant differences appear between the profiles in FIG. 5 and FIG. 6. Thus, it can be seen that the elevations are significantly more pronounced in the systolic phase (FIG. 6) since the walls encountered are thicker due to the contraction of the ventricles. Elevations 910 and 920 have a more pronounced height corresponding to more pronounced thicknesses of the walls, passing through the sampling area. This contraction also causes shrinkage of the cavity 940 internal to the main elevations 910 and 920 corresponding to shrinkage of the internal cavity in the right ventricle.

Figure 7:
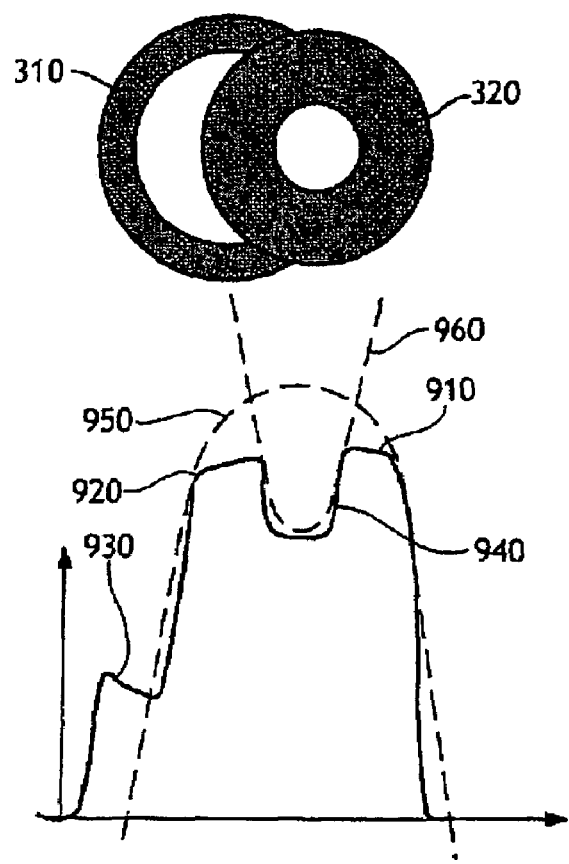
FIG. 7 represents an angiological association between an attenuation profile and analytic curves according to the another embodiment of the invention.

These two modifications of the profile 900 are used (FIG. 7) to output a signal representative of the thickness of the heart walls, and therefore the heart activity. To achieve this, in this case the profile 900 is analysed as being an assembly of two parabolas. The first parabola 950 is considered as being the shape of the external silhouette of the profile. In other words, the external curvature of the two main elevations 920 and 910 is similar to the side of a parabola for which the vertex overhangs the upper cavity 940. The position and curvature of this parabola are identified by automatic shape recognition means integrated into the imagery device processing means. The second parabola 960 corresponds to the curvature and depth of the upper cavity 940. In other words, the inner sides and the bottom of this cavity are considered as defining a parabola (curvature and position). Therefore, the profile 900 defines a pair of parabolas 950 and 960 at each instant, for which the parameters (curvature and position) are unique. When the profile 900 varies during a heart movement, the parabolas 950 and 960 thus positioned vary accordingly.

Other analytic curves could also be adopted, but the parabola is a desirable analytic curve for implementation.

It is also found that the curvature of the external parabola 950 varies accurately as a function of the width of the profile 900, and is consequently a parameter for measuring the distance separating the outside walls of the right ventricle (and more generally the heart). The curvature of the internal parabola 960 represents the width of the internal cavity of the ventricle. Thus, the curvature of the parabola 960 varies as a function of the internal thickness of the heart. These two curvatures are taken into account by making a weighted linear combination of them. In this case this weighted average is a simple difference between these two curvatures. This difference may be considered as being an accurate measurement of the thickness of the ventricle walls.

Figure 8:
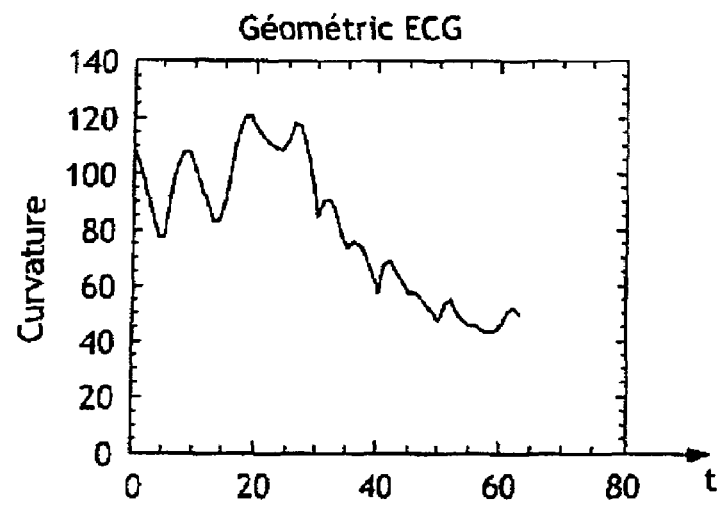
FIG. 8 illustrates the variation of a signal representative of the heart activity obtained in the context of the another embodiment of the invention.

These curvatures thus correspond to the inside and outside radii of curvature of the heart in the area thus observed. It varies with time as shown in the plot in FIG. 8. This variation comprises a series of repetitive peaks corresponding to the systolic phases distributed over a gradual variation corresponding to the injection of a contrast material. However, the contrast material is not necessary for observation of these peaks, and therefore for monitoring the heart activity in itself.

As in the above embodiments, this plot is used to calculate correlation function in order to accurately define the average duration of heart cycles and also to make good use of them in terms of processing synchronous images.

The embodiments of the invention and equivalents thereof may be used in the context of recorded images (particularly after circulation of the contrast material in the arteries network) and in the context of angioscopic images.

The different means described above for efficient monitoring of heart activity are for example controlled by software capable of carrying out the different processing steps when it is implemented on an appropriate processor.

One skilled in the art may make or propose various modifications to the structure/way and/or function and/or results and/or steps of the disclosed embodiments and equivalents thereof without departing from the scope and extant of the invention.

What is claimed is:

1. A method for monitoring cardiac activity comprising:
providing a series of images of the heart by imaging detected attenuation of radiation;
for more than one of the series of images, sampling the attenuation of the radiation on an area subject to repetitive thickenings of at least one wall of the heart;
calculating a weighted linear combination of two curvatures fit to each sampled attenuation; and
analyzing the weighted linear combinations over time to identify a repetitive attenuation signal as a signal representative of the cardiac activity based on a wall thickness of the at least one wall of the heart.

2. The method according to claim 1 wherein the sampling area has an approximately circular periphery approximately corresponding to the dimensions of the heart.

3. The method according to claim 2 wherein the circular periphery surrounds the heart.

4. The method according to claim 3 wherein the sampling area surrounds an area excluded from sampling.

5. The method according to claim 4 wherein the excluded area is an area with regulated intensity.

6. The method according to claim 2 wherein the sampling area surrounds an area excluded from sampling.

7. The method according to claim 6 wherein the excluded area is an area with regulated intensity.

8. The method according to claim 1 wherein the sampling area surrounds an area excluded from sampling.

9. The method according to claim 8 wherein the excluded area is an area with regulated intensity.

10. The method according to claim 1 wherein the sampling area comprises at least one segment that intersects a variable range projection of a wall thickness of the at least one wall of the heart.

11. The method according to claim 10 wherein the segment is oriented at 30° from a longitudinal axis of the heart.

12. The method according to claim 11 wherein the segment is oriented at 60° from a longitudinal axis of the heart.

13. The method according to claim 12 comprising:
providing an attenuation profile on a path of segment(s); and
identifying one or more parameters in an analytic curve of a preset type with a shape conforming to the profile.

14. The method according to claim 13 comprising:
identifying the parameters of two parabolas, one with a shape complying with an external silhouette of the profile, the other with the upper cavity of the profile; and
providing the signal representative of the cardiac activity based on a weighted combination of the parameters of the parabolas, wherein the curvature of at least one of the two parabolas varies as a function of an internal thickness of the heart.

15. The method according to claim 11 comprising:
providing an attenuation profile on a path of segment(s); and
identifying one or more parameters in an analytic curve of a preset type with a shape conforming to the profile.

16. The method according to claim 15 comprising:
identifying the parameters of two parabolas, one with a shape complying with an external silhouette of the profile, the other with the upper cavity of the profile; and
providing the signal representative of the cardiac activity based on a weighted combination of the parameters of the parabolas, wherein the curvature of at least one of the two parabolas varies as a function of an internal thickness of the heart.

17. The method according to claim 10 wherein the segment is oriented at 60° from a longitudinal axis of the heart.

18. The method according to claim 17 comprising:
providing an attenuation profile on a path of segment(s); and
identifying one or more parameters in an analytic curve of a preset type with a shape conforming to the profile.

19. The method according to claim 18 comprising:
identifying the parameters of two parabolas, one with a shape complying with an external silhouette of the profile, the other with the upper cavity of the profile; and
providing the signal representative of the cardiac activity based on a weighted combination of the parameters of the parabolas, wherein the curvature of at least one of the two parabolas varies as a function of an internal thickness of the heart.

20. The method according to claim 10 comprising:
providing an attenuation profile on a path of segment(s); and
identifying one or more parameters in an analytic curve of a preset type with a shape conforming to the profile.

21. The method according to claim 20 comprising:
identifying the parameters of two parabolas, one with a shape complying with an external silhouette of the profile, the other with the upper cavity of the profile; and
providing a signal representative of the cardiac activity based on a weighted combination of the parameters of the parabolas, wherein the curvature of at least one of the two parabolas varies as a function of an internal thickness of the heart.

22. The method according to claim 1 comprising:
providing a plot representative of the cardiac activity; and
providing a correlation relation drawn on this plot, so as to identify at least the average period of beats of the heart.

23. The method according to claim 22 wherein the average heart beat period is used to identify delays or advances of each identified heart beat, on the cardiac activity plot.

24. The method according to claim 22 wherein the delays or advances identified is used to associate synchronous images of different cardiac cycles.

25. A computer readable medium including computer executable code that when executed by a host processor causes the host processor to implement the method according to claim 1.

26. An article of manufacture for use with a computer system, the article of manufacture comprising a computer readable medium having computer readable program code means embodied in the medium, the program code means implementing the method according to claim 1.

27. A program storage device readable by a machine tangibly embodying a program of instructions executable by the machine to perform the method according to claim 1.

28. A radiographic imaging apparatus comprising:
means for monitoring cardiac activity starting from a series of heart images;
means for sampling an attenuation of radiation of more than one of the series of images on an area subject to repetitive thickenings of at least one wall of the heart;
means for calculating a weighted linear combination of two curvatures fit to each sampled attenuation; and
means for analyzing the weighted linear combinations over time to identify a repetitive attenuation signal in this area as a repetitive cardiac activity signal based on a wall thickness of the at least one wall of the heart.

* * * * *